United States Patent
Salyer et al.

(10) Patent No.: US 6,854,742 B2
(45) Date of Patent: Feb. 15, 2005

(54) TOOL DRIVER

(75) Inventors: Paul E. Salyer, Warsaw, IN (US); Todd A. Wolford, Goshen, IN (US); Mark A. Nordman, Burket, IN (US)

(73) Assignee: Symmetry Medical, Inc., Warsaw, IN (US)

( * ) Notice: Subject to any disclaimer, the term of this patent is extended or adjusted under 35 U.S.C. 154(b) by 405 days.

(21) Appl. No.: 09/996,427

(22) Filed: Nov. 19, 2001

(65) Prior Publication Data

US 2002/0099380 A1 Jul. 25, 2002

Related U.S. Application Data

(63) Continuation-in-part of application No. 09/349,381, filed on Jul. 9, 1999, now Pat. No. 6,409,732.

(51) Int. Cl.[7] .............................................. B23B 31/113
(52) U.S. Cl. .................... 279/93; 279/145; 403/349; 606/80
(58) Field of Search .............................. 279/89, 93, 94, 279/104, 143, 145; 403/348, 349; 408/238, 239 R; 606/80, 84, 91, 81, 82; 407/89, 93, 94, 104, 143, 145

(56) References Cited

U.S. PATENT DOCUMENTS

| | | | | |
|---|---|---|---|---|
| 4,906,147 A | * | 3/1990 | Friesinger et al. | 409/232 |
| 5,486,181 A | * | 1/1996 | Cohen et al. | 606/91 |
| 5,582,607 A | * | 12/1996 | Lackman | 606/1 |
| 5,658,290 A | * | 8/1997 | Lechot | 606/80 |
| 5,980,170 A | * | 11/1999 | Salyer | 408/239 R |
| 6,126,359 A | * | 10/2000 | Dittrich et al. | 403/349 |
| 6,179,302 B1 | * | 1/2001 | Gauthier et al. | 279/75 |
| 6,264,647 B1 | * | 7/2001 | Lechot | 606/1 |
| 6,475,221 B1 | * | 11/2002 | White et al. | 606/80 |
| 6,540,739 B2 | * | 4/2003 | Lechot | 606/1 |

* cited by examiner

*Primary Examiner*—Daniel W. Howell
(74) *Attorney, Agent, or Firm*—Taylor & Aust, P.C.

(57) ABSTRACT

A tool driver including a shaft having a longitudinal axis and opposite ends. A first partial boss is located at one of the shaft ends, a tool collet at the other of these shaft ends, and a second partial boss having a bore extending therethrough. The second partial boss being positioned on the shaft with the shaft in the bore. There is a stop on the shaft. The second partial boss is slidable on the shaft between the first partial boss and the stop. A spring is positioned between the second partial boss and the stop. The spring urges the second partial boss into engagement with the first partial boss. The first and second partial bosses are complementary to each other and are in engagement with each other defining a bayonet type latch mechanism. The latch mechanism has an axially extending inwardly tapered bore extending from one end coaxially of the shaft into the first and second bosses. The tapered bore being adapted to receive a coaxially located disc of a tool and to be connected to the tool driver within the tapered bore. The tapered bore and the tool disc coaxially centering the tool on the axis of the tool driver.

46 Claims, 7 Drawing Sheets

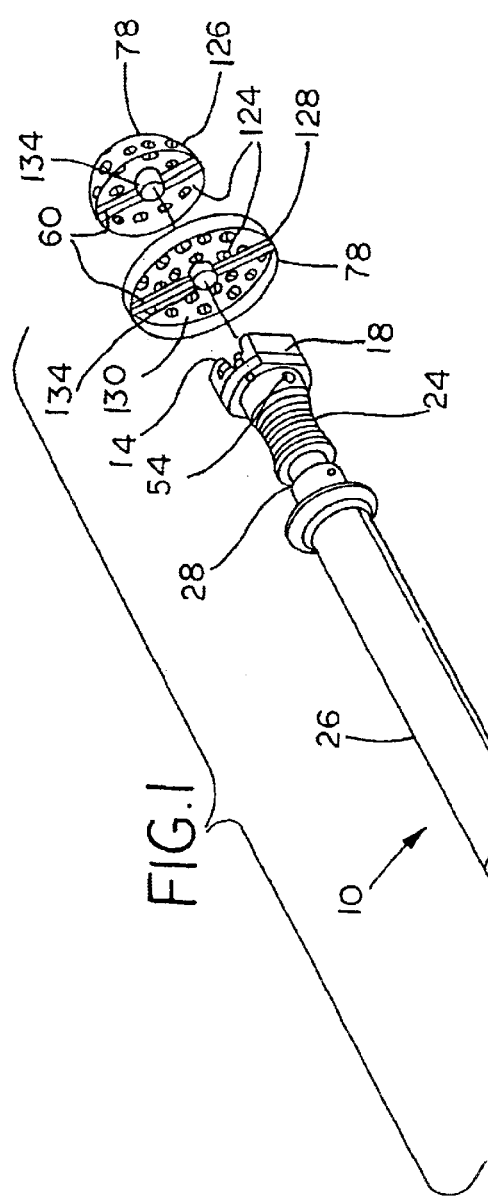
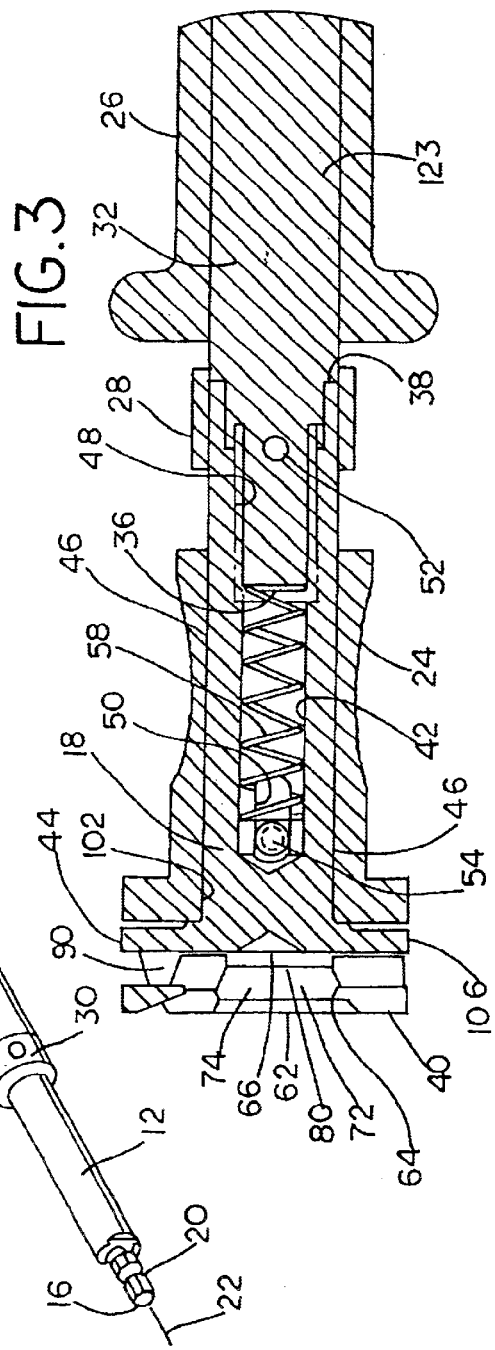

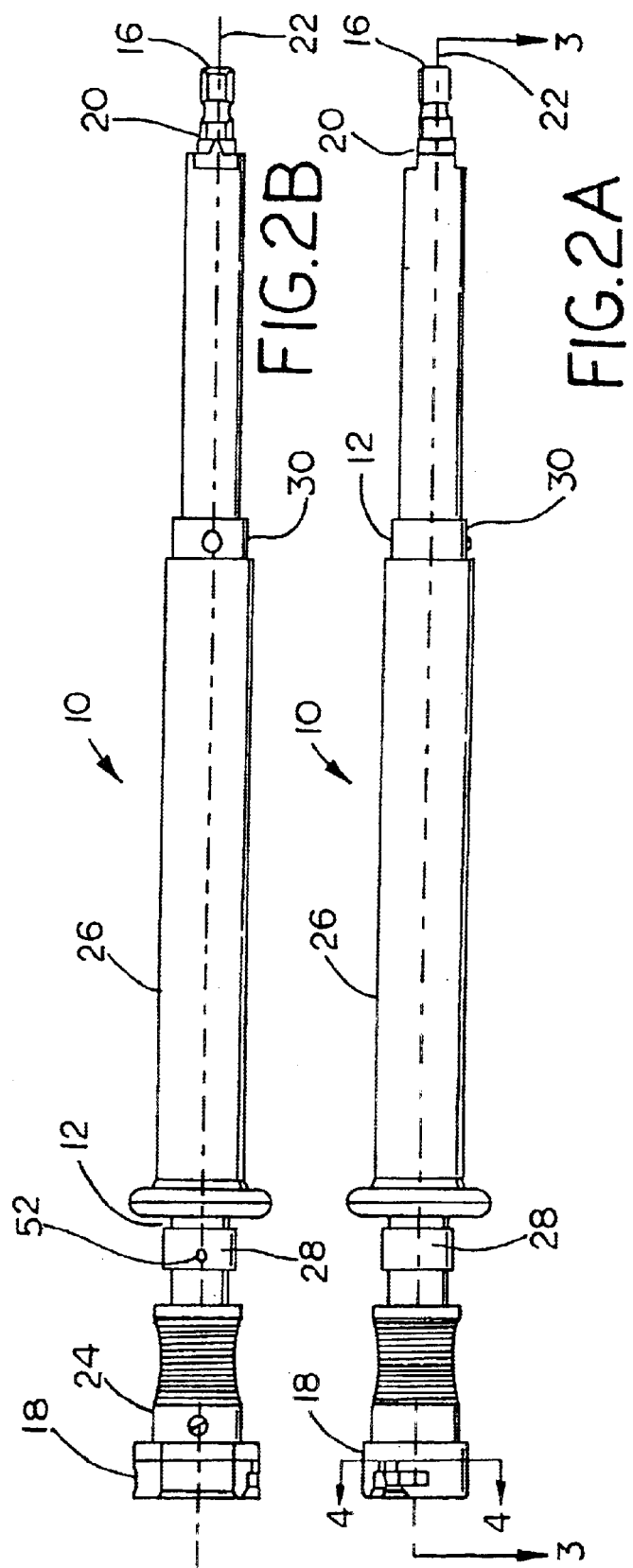

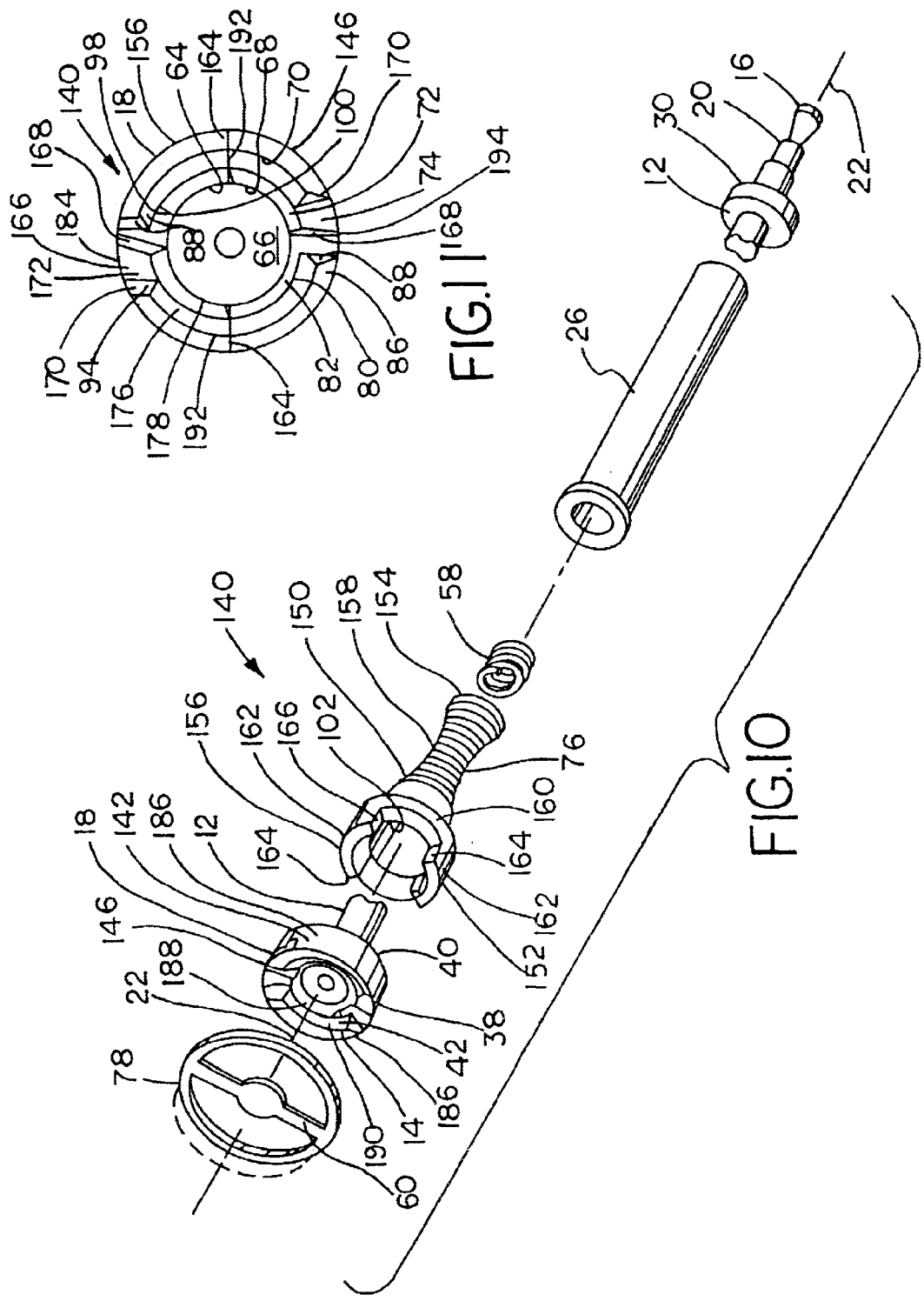

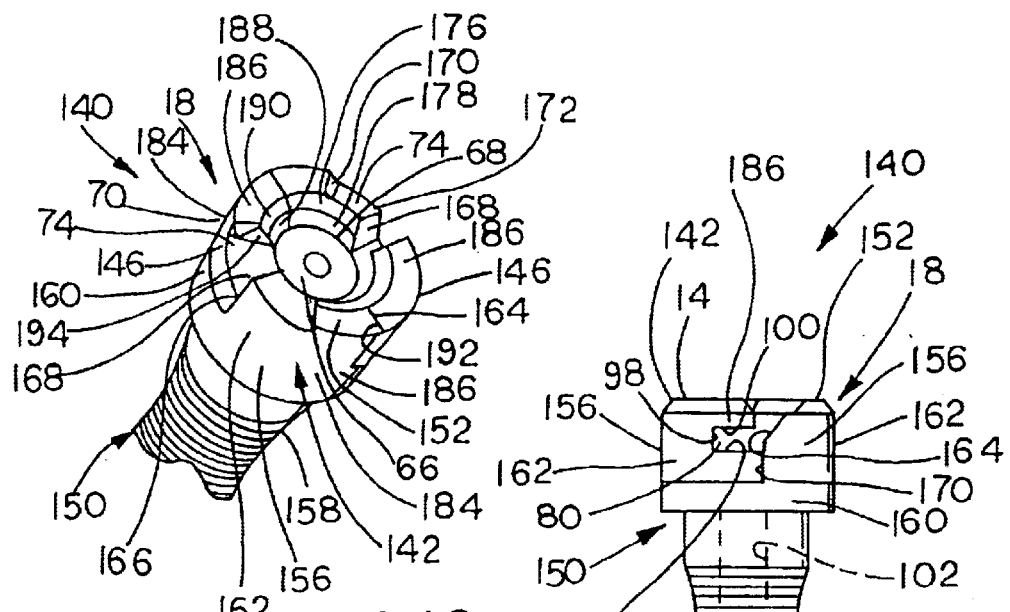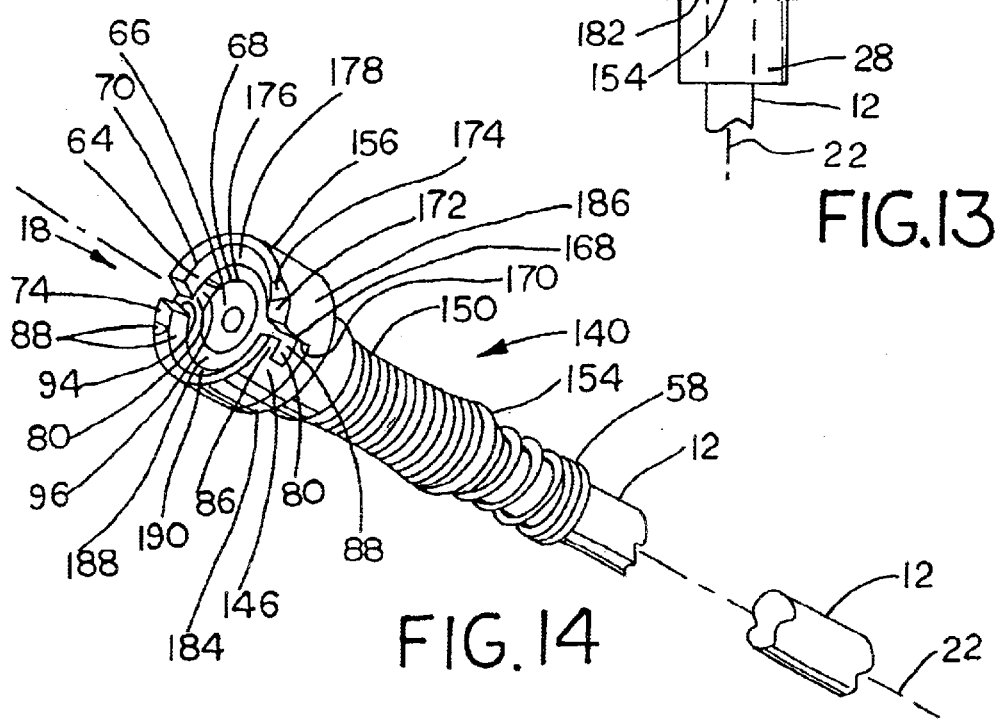

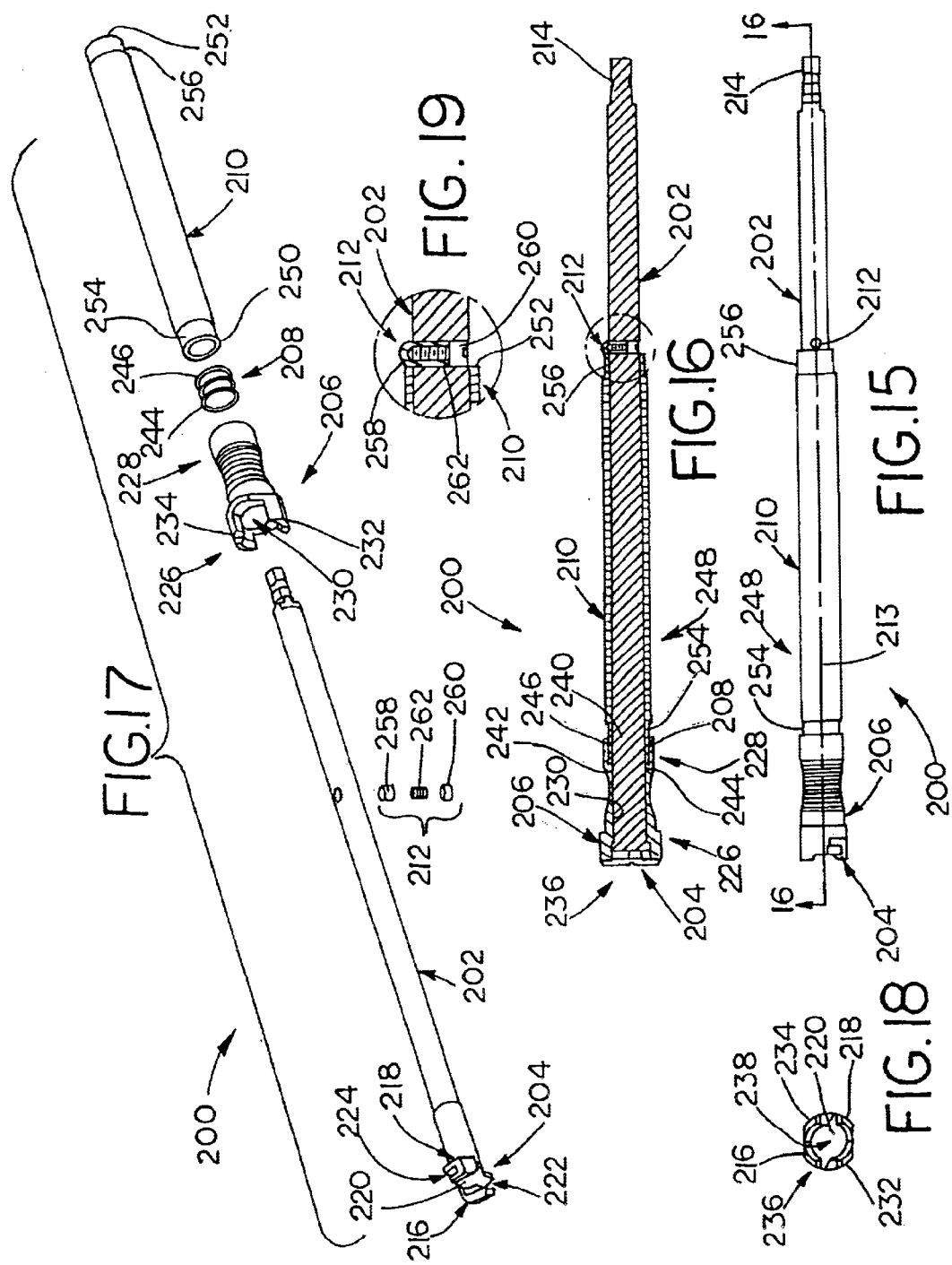

TOOL DRIVER

CROSS REFERENCE TO RELATED APPLICATIONS

This is a continuation-in-part of U.S. patent application Ser. No. 09/349,381, entitled "IMPROVED TOOL DRIVER", filed Jul. 9, 1999 now U.S. Pat. No. 6,409,732.

BACKGROUND OF THE INVENTION

1. Field of the Invention

The present invention pertains to tool drivers and holders for rotary tools, and more particularly, to a new and improved tool driver suitable for driving acetabular reamer cups and patella cutters and glenoid reamers and other surgical tools of any size which is easily cleaned and held and guided to rotate in true concentricity with the tool driver.

2. Description of the Related Art

Patella cutters and acetabular reamer cups and glenoid reamers are surgical tools which are used in surgery for the insertion of artificial joints. Acetabular reamer cups are used to cut hemispherical cavities in pelvis bones for the insertion of artificial hip joints. Patella cutters are used to shape the underside of the patella or knee cap during knee replacement surgery. Glenoid reamers are used to cut hemispherical cavities in shoulder bones for the insertion of artificial shoulder joints. Patella cutters have a complex arrangement of precisely shaped cutting edges arranged around an axis of rotation for cutting the patella. Acetabular reamer cups and glenoid reamers have a complex arrangement of cutting edges arranged on a spherical surface around the axis of rotation of the cup. Acetabular reamers and patella cutters and glenoid reamers perform better when rotated precisely about the axis around which these cutting edges are positioned by design. Additionally precise tolerances cannot be achieved without precise axial rotation as designed.

It is therefore highly desirable to provide a new and improved tool driver. It is also highly desirable to provide a new and improved tool driver which can be used with acetabular reamer cups, patella cutters, glenoid reamers and like rotary tools. It is also highly desirable to provide a new and improved tool driver by which rotary tools may be driven about the tool driver's longitudinal axis with preciseness such that all of the cutting edges of the rotary tool function as designed.

Rotary tools also come in a full range of sizes. Acetabular reamer cups range in size from about 36 millimeters in diameter to about 72 millimeters in diameter. In the past, a specific tool driver could only be used with one or few of the sizes of available tools. Thus, in any operating room there had to be several tool drivers. It is therefore also highly desirable to provide a new and improved tool driver by which acetabular reamer cups and patella cutters and glenoid reamers of all sizes can be driven.

Unique to some knee surgery and some hip operations is the utilization of milled bone, tissue and debris as filler to be placed between the artificial insert and the body to assist the healing process. Thus, acetabular reamer cups and patella cutters and glenoid reamers are mounted on tool drivers in a manner to collect such debris for such use. It is therefore, also highly desirable to provide a new and improved tool driver on which the rotary tools of the type which collect milled bone tissue and other debris for use as filler can be used.

In all surgery utilizing rotary tools, rotary tools such as those driven by rotary tool drivers must be separable from their tool drivers to replace or sharpen as required. It may also be necessary to change tools during an operation, thus, both the rotary tools and the tool drivers must at times be cleaned, sterilized and reused. Thus, it is therefore also highly desirable to provide a new and improved tool driver which can be easily cleaned, sterilized and reused.

Some previous tool drivers grip the tool utilizing opposed pins, flanges and slots, or opposed spring loaded ball catches, or other such devices. These devices represent a problem in that the catches tend to trap dried blood and other debris which are very difficult to remove during a cleaning process. It is therefore also highly desirable to provide a new and improved tool driver which is simple in construction, easy to use and does not have opposed pins, flanges, slots and other devices in which to catch debris and render the tool driver difficult to clean, sterilize and reuse.

An additional problem is that unless tolerances of tools and tool drivers are made very close, at a greatly increased cost, there is considerable free play between the tool and the tool driver. This increased play increases the wear of the cutting edges, makes more difficult the positioning of the tool, renders the tool useless for holding close tolerances, requires the tool not to cut as designed, and there is no possibility of utilizing the rotary tool spinning precisely about its axis as designed. It is therefore, also highly desirable to provide a new and improved tool driver which allows the rotary tool to be utilized spinning precisely about its axis, as designed.

It is also highly desirable to provide a new and improved tool driver in which close tolerances can be held.

Finally, it is highly desirable to provide a new and improved tool driver which has all of the above desired features.

SUMMARY OF THE INVENTION

It is therefore an object of the invention to provide a new and improved tool driver.

It is also an object of the invention to provide a new and improved tool driver which can be used with both acetabular cups, patella cutters, glenoid reamers and like rotary tools (i.e., orthopedic implant preparation tools).

It is also an object of the invention to provide a new and improved tool driver by which rotary tools may be driven about the tool drivers longitudinal axis with preciseness such that all of the cutting edges of the rotary tool function as designed.

It is also an object of the invention to provide a new and improved tool driver which acetabular reamer cups of all sizes and patella cutters and glenoid reamers can be driven.

It is also an object of the invention to provide a new and improved tool driver on which the rotary tools of the type which collect milled bone tissue and other debris for use as filler, can be used.

It is also an object of the invention to provide a new and improved tool driver which can be easily cleaned, sterilized and reused.

It is also an object of the invention to provide a new and improved tool driver which allows the rotary tool to be utilized spinning precisely about its axis as designed.

It is also an object of the invention to provide a new and improved tool driver which is simple in construction, easy to use and does not have opposed pins, flanges, slots and other devices in which to catch debris and render the tool driver difficult to clean, sterilize and reuse.

It is also an object of the invention to provide a new and improved tool driver in which close tolerances can be held.

It is finally an object of the invention to provide a new and improved tool driver which has all of the above desired features.

In the broader aspects of the invention there is provided a new and improved tool driver having a shaft with a longitudinal axis and opposite ends, a boss is secured at one of the shaft ends by which the tool driver is connected to a rotary tool. A tool collet is secured to the other of the shaft ends by which the tool driver may be driven by a surgical hand piece having a chuck in which the collet may be positioned. The boss is equipped with a securing device of the bayonet type having a latch mechanism which holds the rotary tool on the boss coaxially of the driver during use. In a specific embodiment, the tool driver boss comprises a first partial boss secured to the shaft. A second partial boss having a bore extending therethrough is positioned on the shaft. A stop is positioned on the shaft and a spring is positioned on the shaft between the stop and the second partial boss. The spring urges the two partial bosses together. The partial bosses are moveable from a closed position in which the two bosses are complementary and fully define the boss of the tool driver to an open position in which the two partial bosses are separated. When the two partial bosses are in their closed complementary position, the boss defines a tapered bore extending from the distal end of the boss axially of the shaft. The rotary tool has a diametral bar extending across a bottom tool driver opening with a centrally located circular disc therein. The disc of the rotary tool fits within the bore of tool shaft boss so as to concentrically locate the rotary tool and the tool shaft on the same axis. The latch mechanism holds the tool driver and the tool together in this position, whereby rotary tools of a multitude of sizes can be secured concentrically to the tool shaft when the two partial bosses are separated against the urging of the spring and in their open position, the rotary tool may be placed within and removed from the bayonet type securing device and latch mechanism.

BRIEF DESCRIPTION OF THE DRAWINGS

The above-mentioned and other features and objects of the invention and the manner of attaining them will become more apparent and the invention itself will be better understood by reference to the following description of an embodiment of the invention taken in conjunction with the accompanying drawings wherein:

FIG. 1 is an exploded perspective view of the tool driver of the invention showing two sizes of acetabular reamer cups and patella cutters exploded therefrom, illustrating the versatility of the new and improved tool driver of the invention;

FIGS. 2A and 2B are side views of the new and improved tool driver of the invention illustrated in FIG. 1 taken perpendicularly with respect to each other;

FIG. 3 is a fragmentary sectional view of the new and improved tool driver of the invention illustrated in FIGS. 1 and 2 taken along the section line 3—3 of FIG. 2A;

FIG. 10 is an exploded fragmentary perspective view of a modified version of the tool driver of the invention showing the shaft and the partial boss or head secured to the shaft and the trigger with the partial boss secured to the trigger;

FIG. 11 is a top planar view of the tool driver of the invention illustrated in FIG. 10 with the partial bosses of both the head and the trigger complementary assembled;

FIG. 12 is a fragmentary perspective view of the head and shaft of the assembled new and improved tool driver of the invention shown in FIG. 10 from a direction 90° opposite that shown in FIG. 10;

FIG. 13 is a fragmentary side view of the tool driver of the invention in its complementary assembled condition as shown in FIG. 1;

FIG. 14 is a fragmentary perspective view of the trigger of the assembled new and improved tool driver of the invention illustrated in FIG. 10 from a direction 90° opposite that shown in FIG. 10;

FIG. 15 is a partial break away, side view of another embodiment of a tool driver of the present invention;

FIG. 16 is a cross-sectional view taken along section line 16—16 of the tool driver shown in FIG. 15;

FIG. 17 is an exploded view of the tool driver shown in FIG. 15;

FIG. 18 is an end view of the tool driver shown in FIG. 15; and

FIG. 19 is an enlarged view of the bias button and surrounding portion of the tool driver shown in FIG. 16.

DETAILED DESCRIPTION OF THE INVENTION

Figure 4:
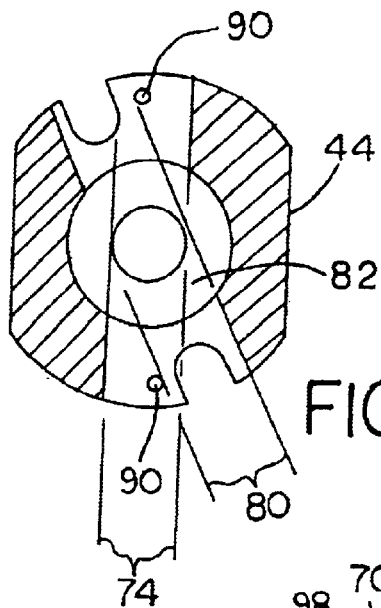
FIG. 4 is a cross-sectional view of the new and improved tool driver of the invention illustrated in FIGS. 1–3 taken substantially along the section line 4—4 of FIG. 2A.

Tool driver 10 comprises a shaft 12 having opposite ends 14, 16 as shown in FIG. 1. At end 14, a boss or head 18 is secured to the shaft 12. At end 16, a tool collate 20 is secured to shaft 12. Shaft 12 has an elongated axis 22 about which both boss or head 18 and collate 20 are positioned and rotated during use. Boss or head 18, collate 20 and shaft 12 are coaxially aligned in end to end relation. Coaxially positioned on the shaft 12 is a tubular trigger 24 and a handle 26. Handle 26 is free to rotate about the shaft 12 between a pair of spaced apart rings 28 and 30 (ring 30 may be optional) which are secured to shaft 12.

Shaft 12 is made up of head 18, a rod 32 and collate 20. Rod 32 has opposite ends 34 and 36. Similarly, head 18 has opposite ends 38, 40. Head 18 at end 38 has a bore 42 extending axially of head 18. Head 18 has a boss 44 at end 40 and a tubular portion 46 extending from boss 44 to end 38. Bore 42 extends from end 38 to adjacent boss 44. A slot 50 extends transversely of the tubular portion 46 adjacent boss 44 through the bore 48. Slot 50 is elongated in an axial direction as shown.

End 36 of rod 32 is shaped so as to be telescopically received in bore 48 adjacent end 38 of head 18. Rod 32 is secured to head 18 by a pin 52 extending through hole 53 and secured at its opposite ends in ring 28. In other specific embodiments, head 18 and rod 32 or rod 32 and ring 28 may be integrally formed as a single piece. A second pin 52 extends through the ring 30 in the manner above described with regard to the attachment of the head 18 to the rod 32 by ring 28 to secure ring 30 to rod 32 remote from ring 28. Positioned on rod 32 between rings 28 and 30 is tubular handle 26. Handle 26 is coaxial of the rod 32 and is free to rotate independently of rod 32 and to move axially of rod 32 between rings 28, 30.

Similarly positioned on tubular portion 46 of head 18 is trigger 24. Trigger 24 is also free to slide axially of tubular portion 46 between boss 44 and ring 28 except for the engagement of a pin 54 which extends through trigger 24, through slot 50 in head 18, and is secured at its opposite ends to trigger 24.

Figure 6:
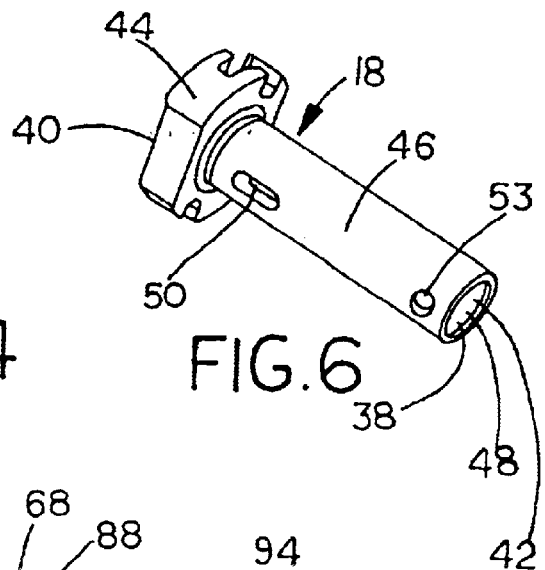
FIG. 6 is a perspective view of the head of the new and improved tool driver of the invention illustrated in FIGS. 1–5.

A spring 58 is positioned within bore 42 of head 18 and compressed between end 36 of rod 32 and pin 54. In a specific embodiment where head 18 and rod 32 are integral, spring 58 is positioned about shaft 12 between trigger 24 and ring 28. Pin 54 limits the movement of trigger 24 on tubular portion 46 of head 18 both rotatably about tubular portion 46 and axially of tubular portion 46. See FIGS. 3 and 6.

Figure 5:
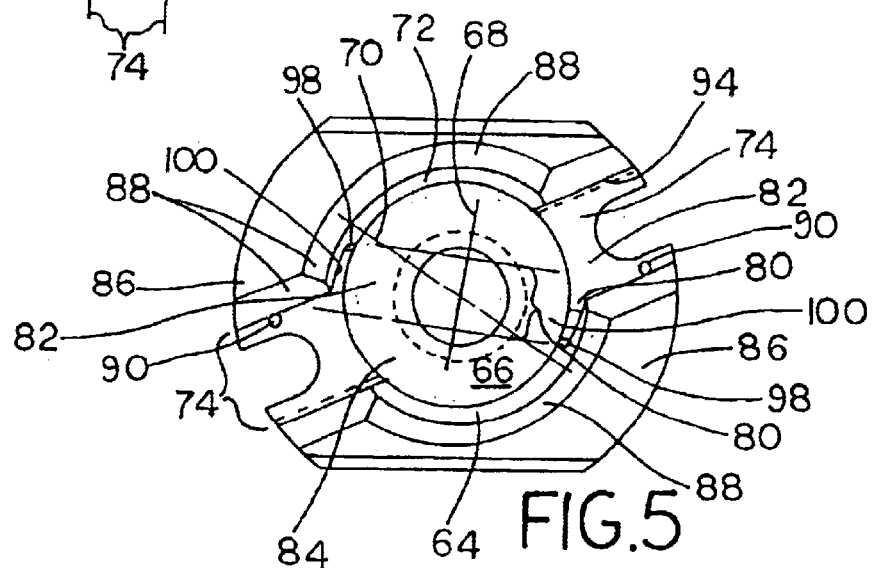
FIG. 5 is a top planar view of the head of the new and improved tool driver of the invention illustrated in FIGS. 1–4.

Boss 44 of head 18 has a distal end 62 and a bore 64 extending axially from distal end 62 of head 18. Bore 64 is tapered as shown in FIGS. 3 and 5 so as to have a bottom 66, a bottom diameter 68, a top diameter 70 and tapered side walls 72. A groove 74 is machined in boss 44 so as to extend diametrically across bore 64 and to have a width which is equal or larger than the diametral rod or bar 60 of the tool 78 which will be used with the tool driver 10. A second diametral groove 80 extends across the bore 64 with a bottom 82 in the same plane as the bottom 84 of the groove 74 and the bottom 66 of the bore 64. Groove 80 is overlaid with a portion 86 of the distal end of the head 18 to form a bayonet-type latch. See FIGS. 4 and 5. Groove 74 and bore 64 both have a peripheral tapered surface 88 defining the entry of both bore 64 and groove 74. Bottom 82, 84 have holes 90 therein extending through the head 18 to receive the pins 92 on trigger 24. Groove 74 is bounded on one side by a side wall 94 and on the other side by groove 80. Groove 80 has a floor or bottom 96 in the same plane as bottoms 66, 82 and 84, an upstanding side wall 98, and a ceiling 100. Bottom 96 and ceiling 100 are tapered toward side wall 98 as will be explained hereinafter.

Figure 7:
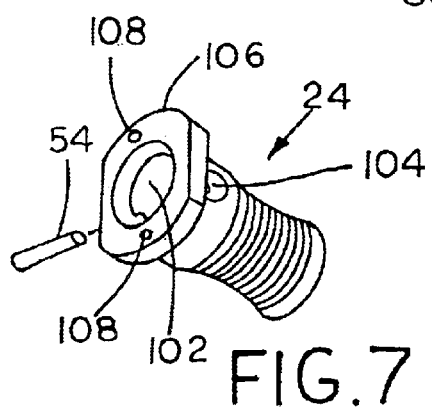
FIG. 7 is a perspective view of the trigger of the new and improved tool driver of the invention illustrated in FIGS. 1–5.
Figure 8:
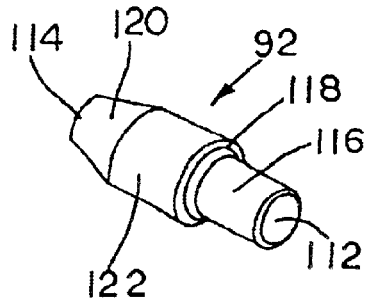
FIG. 8 is a perspective view of the pins which are secured to the trigger of the new and improved tool driver of the invention and which extend upwardly through the head of the new and improved tool driver of the invention.
Figure 9:
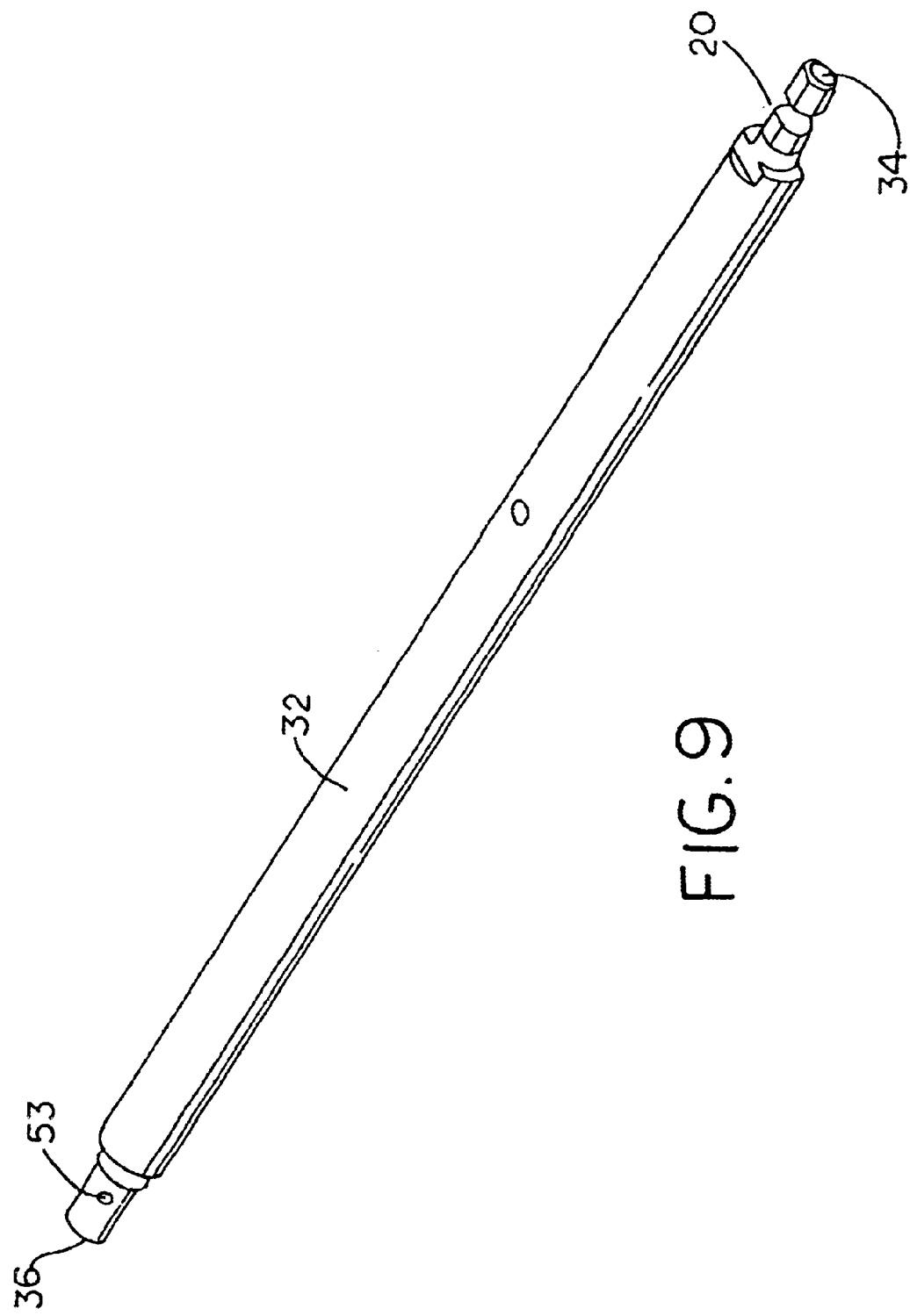
FIG. 9 is a perspective view of the shaft to which is secured the head and on which the trigger and handle is assembled.

As shown in FIGS. 3 and 7, trigger 24 has a bore 102 extending axially therethrough. Transversely of trigger 24 is a pin bore 104 in which the opposite ends of pin 54 are secured. Trigger 24 is slideably mounted upon tubular portion 46 of head 18. Portion 46 is positioned within bore 102. Trigger 24 has a boss 106 which is urged by the spring 58 against boss 44 of the head 18. In the distal end of boss 106 are a pair of diametrically opposed pin bores 108. Pin bores 108 extend axially of trigger 24, and pin bores 108 are positioned with respect to each other such that when pin 54 attaches trigger 24 to head 18, pin bores 108 are coaxial with the pin bores 90 of boss 44 of head 18.

Pins 92 are positioned in pin bores 108. Pins 92 have opposite ends 112, 114. At end 112 is a shank 116 which is secured within a pin bore 108. Shank 116 extends from end 112 and terminates at step 118. Adjacent the opposite end 114 is a tapered surface 120, the purpose of which will be mentioned hereinafter. Between tapered surface 120 and shank 116 is a cylindrical pin portion 122 which is slideably positioned within pin bores 90 of head 18 and boss 44 of head 18. See FIG. 3.

In a specific embodiment, rod 32 is from about 7 to about 11 inches in axial length, has a diameter of approximately 0.375 inches in diameter and made of stainless steel. Handle 26 is from about 5 to about 5.5 inches in length. Bore 123 therethrough is approximately 0.5 inch in diameter. Handle 26 is made of molded polyethylene. Trigger 24 is from about 1.25 inches to about 1.5 inches in axial length, and has a diameter from about 0.375 to about 1.25 inches in diameter and bore 48 extending therethrough is about 0.5 inches in diameter. The pin holes 108 are about 0.1 inches in diameter. Pins 90 are approximately 0.431 inches in diameter. Both trigger 24 and pins 90 are made of stainless steel. Head 18 is approximately 2½ inches long with boss 44 having an axial length of about 1.0625 inches. Head 18 is machined from stainless steel. Bore 48 in tubular portion 46 is approximately 0.25 inches in diameter and bore 64 is approximately 0.550 inches in diameter with a top diameter of 0.637 and a bottom diameter of 0.550 inches. Slot 50 has a width of about 0.125 inches and groove 80 has a width of approximately 0.266 inches. The outside diameter of boss 44 is approximately 1 inch.

In a specific embodiment, diametral rod or bar 60 of the tool 78 is approximately 0.26 inches in width, approximately 0.125 inches in thickness and has a diametral length commensurate with the diameter of the tool 78. The central disc 134 of rod 60 has a diameter of about 0.550 inches and a thickness of about 0.125 inches.

Referring now to FIG. 1, the rotary tool 78 of tool driver 10 is shown to have a hollow interior 124. The rotary tool 78 can be either an acetabular reamer 126 or a patella cutter 128. Each of the rotary tools 78 have a rear opening 130 which provides access to the interior 124 such that milled bone, tissue and other debris may be collected within the interior 124 and removed for use during the surgical procedure as desired. Each of the rotary tools has extending across the opening 130 a diametral bar or rod 60. Equally distant between the ends of the diametral bar 60 is a centering disc 134. Centering disc 134 has a diametral relationship with bore 64, and diametral bar 60 has a diametral relationship with both grooves 74, 80 as will be mentioned hereinafter. Rotary tools 78 are provided in a variety of sizes ranging from 36 millimeters in diameter to 72 millimeters in diameter. Each of these rotary tools, however, have a diametral mounting bar 60 and a centering disc 134 of the same dimensions for reasons to become clear hereinafter.

In operation, the rotary tool 78 to be driven by the tool driver 10 is selected and positioned adjacent the distal end 62 of the boss 44. The diametral mounting bar or rod 60 is aligned with groove 74 and moved axially toward end 16 of the shaft 12. Diametral bar 60 may engage the taper 88 and be guided by the taper 88 into the groove 74. Groove 74, between pin 90 and the groove side 94 opposite pin 90, has a sufficient width to accommodate the bar 60. The centering disc 134 is dimensioned with respect to the bore 64 such that it centers the bore 64 and the centering disc 134 of the tool 78 and positions the tool 78 and the shaft 12 coaxially on axis 22, the axis of rotation of the shaft 12. Thus, the diametral periphery of the centering disc 134 may engage the taper 88 and then the wall 72 of the bore 64 to be guided into its coaxial position and to rest on the bottom 66 or thereabouts. Inasmuch as the groove 74 does not have tapered walls, but the bore 64 does, the difference in the top diameter 70 and the bottom diameter 68 of the bore 64 will function with the centering disc 134 to center the tool 78 coaxially of the shaft 12.

The taper of the bore 64 centers the tool 78 coaxially of the shaft 12 irrespective of the holding of tolerances of either the bore 64 or the centering disc 134. Even if tolerances are held loosely, the tapered sides of bore 64 between the bottom diameter 68 and the top diameter 70 center the centering disc 134 on the axis 22 and position the centering disc coaxially of the shaft 12. Different dimensions of the bore 64 or the centering disc 134 within loose tolerances would position the centering disc 134 at various positions spaced apart from bore bottom 66. However, in each of these positions, the centering disc 134 and the rotary tool 78 would still be coaxial of the shaft 12.

Once the centering disc 134 and the diametral bar 60 are positioned within bore 64 and groove 74, respectively, pins 92 may be retracted by moving the trigger 24 toward end 16 against the resiliency of the spring 58. By moving the trigger 24, the pin 54 is moved toward the end 36 of shaft 12, compressing the spring 58 and retracting the pins 92 into the pin holes 90. With pins 92 retracted, the tool 78 can be rotated with respect to the shaft 12 so as to move the diametral bar 60 from groove 74 into the bayonet-type catch 136 defined by groove 80, its bottom 82, its overlaying portion 86, upstanding groove wall 98 and top wall 100. Bottom 82 and top wall 100 are also tapered, again to make unnecessary close tolerances, and to hold bar 60 against axial movement therebetween.

Diametral bar 60 can then be held fast within the bayonet catch 136 by releasing the trigger 24 and allowing the spring 58 to urge the trigger 24 against the boss 44 to move the pins 92 back into their at rest position. Pins 92, and specifically the tapered portions 120 thereof, engage the diametral bar 60 and urge the diametral bar 60 toward the wall 98 of the groove 80. By its tapered portion 120, pins alleviate any need for holding close tolerances between the wall 98 and the pin holes 90 or in the width of the diametral bar 60. Additionally, the tolerances between wall 100 and bottom 82 of groove 80 need not be held close, as well as the tolerances of the dimensions of the diametral bar 60, the tolerances between bottom 82 and top wall or ceiling 100, the tolerances between the centering disc 134 and the bore 64, and the tolerances between the diametral bar 60 and the opposite walls 98 of the groove 80 and the tapered pin portion 120 to hold the rotary tool 78 coaxially of the shaft 12 and immovable relative to shaft 12. Because of the taper of the bore 64 and the taper of the pin 92, lateral movement of the tool 78 with respect to the shaft axis 22 and rotary movement about the shaft axis 22 of the tool 78 is prevented. Axial movement of the diametral bar 60 is prevented by the taper between wall 100 and bottom 82 of groove 80. Thus, no close tolerances are necessary in the manufacture of the rotary tool driver 10 of the invention.

To release the rotary tool 78 of the invention from the new and improved tool driver 10 of the invention, the process is reversed. The trigger 24 is urged against spring 58 toward end 36 of the rod 32 withdrawing the pins 92 into the pin holes 90, the rotary tool 78 is rotated about the axis 22 so as to position the diametral bar 60 in the groove 74 and the rotary tool 78 can then be separated by moving the rotary tool relative to the tool driver 10 axially thereof and a new rotary tool 78 can be installed as above described.

Referring to FIGS. 10–14, a modified version 140 of the tool driver 10 is shown. Tool driver 140 comprises a shaft 12 having opposite ends 14, 16. At end 14, a boss or head 142 is secured to shaft 12. At end 16, tool collet 20 is secured to shaft 12. Shaft 12 has an elongated axis 22 about which both boss or head 142, collet 20 and shaft 12 are coaxially aligned in end to end relation. Coaxially positioned on the shaft 12 is a trigger 150 and a handle 26. Handle 26 is free to rotate about the shaft 12 between a pair of spaced apart rings 28 and 30 which are secured to shaft 12.

Shaft 12 is made up of part head 146 and collet 20. Shaft 12, part head 146 and collet 12 may be integrally formed by machining the same from a single piece of material. Part head 146 has opposite ends 38, 40. Part head 146 at end 38 has a bore 42 extending axially of part head 146. Spaced apart rings 28, 30 are secured to shaft 12 as above described. Positioned on shaft 12 between rings 28 and 30 is tubular handle 26. Handle 26 is coaxial of shaft 12 and is free to rotate independently of shaft 12 and to move axially of shaft 12 between rings 28, 30. Similarly positioned on shaft 12 is trigger 150. Trigger 150 is also free to slide axially of shaft 12 between part head 146 and ring 28. A spring 58 is positioned between trigger 150 and ring 28. Spring 58 urges trigger 150 in contact with part head 146.

Trigger 150 has a bore 102 extending axially therethrough. Trigger 150 has opposite ends 152, 154. Adjacent end 152 is a part boss 156. Adjacent end 154 is a thumb groove 158. Trigger 150 is mounted on shaft 12 between ring 28 and part head 146. Spring 58 urges part boss 156 into engagement with part head 146. When engaged, part boss 156 and part head 146 form boss 18. Thus, part head 146 and part boss 156 are complimentary to each other. When part head 146 and part boss 156 are positioned together in complimentary position 184, part head 146 and part boss 156 define bore 64, groove 74 and groove 80 as above described.

Part boss 156 comprises a disc 160 through which concentrically positioned bore 102 passes. Diametrically opposite each other and upstanding from disc 160 are two pillars 162 which are identical in all respects. Pillars 162 have a pillar wall 164, at least a portion of which is angled relative to disc 160 to aid insertion of tool 78, and opposite upstanding wall 166. Wall 166 is fragmented into a lower planar portion 168 which is generally perpendicularly aligned to disc 160, an upper planar portion 170 which is tapered inwardly of pillars 162, a generally planar surface 172 which is generally parallel to the surfaces of disc 160 and a planar surface 174 which is again tapered inwardly of pillars 162. The taper of surface 174 is more severe than the taper of surface 170. See FIGS. 11 and 12.

Interior surfaces 176 and 178 of pillars 162 define a part of bore 64 and are tapered to define a bottom 66, bottom diameter 68, top diameter 70 and tapered side walls 72 as afore described. Internal conical surfaces 176, 178 define bore 64 in full when part head 146 and part boss 156 are assembled in their complimentary position 184. Extending from part boss 156 is tubular portion 76 through which bore 102 extends from end 152 to end 154 and thumb groove 158 circumferentially extends. Extending from end 154 is bore 182. Bore 182 cooperates with ring 28 to enclose spring 58.

Part head 146 is secured to end 14 of shaft 12. Part head 146 also includes a pair of diametrically opposed pedestals 186 secured on opposite sides of shaft 12. Pedestals 186 are also identical, and thus, the description of one will suffice for the other. Pedestals 186 are spaced apart by bottom 66 of bore 64 as described above. Each pedestal 186 has an interior surface 188 adjacent to bottom 66 and an upper interior surface 190. Surfaces 188 and 190 are tapered as above described with regard to surfaces 176 and 178 and tapered side walls 172. Surfaces 176, 178, 188 and 190, when part head 146 and part boss 156 are put together in complimentary position 184, define bore 64 to have bottom 66, a bottom diameter 68, a top diameter 70 and tapered walls 72 as above described. Pedestals 186 also have an upstanding, generally perpendicular planar side wall 192 which is complimentary to pillar wall 164 when part head 146 and part boss 156 are positioned together in complimentary position 184. Pedestal 186 has an opposite, generally perpendicular upstanding side wall 194 into which diametral groove 80 extends into. Groove 80 has bottom 82 in the same plane as bottom 66 and is overlaid with portion 86 to form a bayonet-type latch. Opposite side wall 194 is complimentary to surfaces 168 and 170 when part head 146 and part boss 156 are put together in complimentary position 184. Pedestals 186 are separated by groove 74 which extends diametrically across bore 64 and has a width which is equal or larger than the diametral rod or bar 60 of the tool 78 which will be used with the tool driver 140. Groove 74 and bore 64 both have a peripheral tapered surface 88 defining the entry of both bore 64 and groove 74 when part head 146 and part boss 156 are put together in complimentary position 184. Groove 74 is bounded on one side by a side wall 94 and on the other side by groove 80. Groove 80 has a bottom 96 in the same plane as bottoms 66, 82 and 84 and upstanding side wall 98 and a ceiling 100. Bottom 96 and ceiling 100 are tapered toward side wall 98 as explained above. Tapered wall 170 of pedestals 162 act in conjunction with tapered bottom 96 and ceiling 100 to wedge rod or bar 60 of the tool 78 which is secured to the tool driver 140 in groove 80 as desired.

When part head 146 and part boss 156 are placed together in complimentary position 184, they form boss or head 18 as above described. Because of the tapers of bottom 96 and ceiling 100 and side wall 166, whenever a rod or bar 60 of the tool 78 is positioned in groove 80, part head 146 and part boss 156 are held in a partially complimentary position 196 by spring 58. The tapers of bottom 96, ceiling 100 and side wall 166 wedge bar 60 and tool 78 in groove 80 and hold tool 78 fast in a totally coaxial position with regard to shaft 12. How closely the partially complementary position 196 is to complementary position 184 depends upon the tolerances of tool 78 and part bosses 146, 156.

In a specific embodiment, rod 32 is from about 7 to about 11 inches in axial length, has a diameter of approximately 0.375 inches in diameter and made of stainless steel. Handle 26 is from about 5 to about 5.5 inches in length. Bore 123 therethrough is approximately 0.5 inch in diameter. Handle 26 is made of molded polyethylene. Trigger 24 is from about 1.25 inches to about 1.5 inches in axial length, and has a diameter from about 0.375 to about 1.25 inches in diameter and bore 48 extending therethrough is about 0.5 inches in diameter.

In operation, the rotary tool 78 to be driven by tool 140 is selected and positioned adjacent the distal end 62 of the boss 44. The diametral mounting bar or rod 60 is aligned with the groove 74 and moved axially toward end 16 of the shaft 12. Diametral bar 60 may engage the taper 174 and be guided by the taper 174 into groove 74. Groove 74 between side 192 and 194, has sufficient width to accommodate bar 60. The centering disc 134 is dimensioned with respect to the bore 64 such that it centers the bore 64 and the centering disc 134 of the tool 78 and positions the tool 78 on the shaft 12 coaxially on axis 22, the axis of rotation of the shaft 12. Thus, the diametral periphery of the centering disc 134 may engage the taper 88 and then walls 72, initially tapered surface 190 and subsequently tapered surface 188 of the bore 64 to be guided into its coaxial position and to rest on bottom 66 or thereabouts. Inasmuch as the groove 74 does not have tapered walls, but the bore 64 does, the difference in the top diameter 70 and the bottom diameter 68 or the bore 64 will function with the centering disc 134 to center the tool 78 coaxially of the shaft 12.

Once the centering disc 134 and the diametral bar 60 are positioned within the bore 64 and groove 74, respectively, the trigger 24 may be moved toward end 16 against the resiliency of the spring 58. By moving the trigger 24, part boss 156 is moved toward end 16 allowing centering disc 134 to approach bottom 66 of bore 64 and diametral bar 60 to rest on the bottom of groove 74. In this position, tool 78 can be rotated with respect to the shaft 12 so as to move the diametral bar 60 from groove 74 into the bayonet-type catch 136 defined by groove 80, its bottom 82, its overlaying portion 86, upstanding groove wall 98 and ceiling 100. Bottom 82 and ceiling 100 are tapered, again to make unnecessary close tolerances, and to hold bar 60 against axial movement.

Diametral bar 60 can then be held fast within bayonet-type catch 136 by releasing trigger 24 and allowing the spring 58 to urge the trigger 24 and part boss 156 into its complimentary position 184 with part head 146. Surface 170 then engages diametral bar 60 and forces diametral bar 60 against its taper toward wall 98 of the groove 80 against the taper of bottom 82 and ceiling 100. By its tapered portion, tapered wall 170, there is no need for holding close tolerances between the wall 98 and wall 170 or the width of the diametral bar 60. Additionally, the tolerances between ceiling 100 and bottom 82 and groove 80 need not be held close as well as the tolerances of the dimensions of the diametral bar 60, the tolerances between bottom 82 and ceiling 100, the tolerances between the centering disc 134 and the bore 64 and the tolerances between diametral bar 60 and the opposite walls 98 of the groove 80. Because of these tapered surfaces, the rotary tool 78 will always be held coaxially of the shaft 12 and immoveable relative to the shaft 12, both in radial directions and axially without close tolerances.

To release the rotary tool 78 of the invention from the tool driver 140, the process is reversed. The trigger 24 is urged against spring 58 toward end 16 of shaft 12 and the rotary tool 78 is rotated about axis 22 from groove 80 into groove 74. With the diametral bar 60 of the tool 78 in groove 74, the rotary tool 78 can then be separated from the tool driver 140 by moving the rotary tool relative to the tool driver 140 axially thereof, and a new rotary tool 78 can be installed as above described.

Tool drivers 10 and 140 may be totally "field strippable" for sterilization purposes whenever desired, by utilizing pins 52 and 54 which are removable whenever desired. By removing the pin 52 which secures ring 30 to rod 32, ring 30 may be removed from rod 32 and tubular handle 26 may be removed from rod 32 by passing ring 30 and handle 26 over collate 20. Similarly, by removing pin 52 which secures ring 28 to rod 32 and secures head 18 and rod 32 together, head 18, part heads 146, 156, rod 32, shaft 12, spring 58 and ring 28 may be disassembled into separate integral pieces. Similarly, by removing pin 54, triggers 24 and 150 can be disassembled from head 18 and part head 146, respectively.

Once totally disassembled, tool driver 10 is in a number of pieces that can be easily cleaned and sterilized. The sterilized pieces can than be easily reassembled by repositioning pins 52 and 54 as disclosed. In a specific embodiment, pins 52 and 54 may be conventional screws having a head at one end and threads at the opposite end. Alternatively, pins 52 and 54 may be any of the removable pins taught in the prior art.

Another embodiment of the present invention, is best shown in FIGS. 15–17. Tool driver 200 includes a driver shaft 202 with a first partial boss 204 at one end thereof; a second partial boss 206; a shaft spring 208; a driver sleeve 210; and a bias button 212.

Driver shaft 202 has a longitudinal shaft axis 213 and includes first partial boss 204 defining one end thereof and a tool collect 214 defining the other. First partial boss 204 has first latch member 216, a diametrically opposed second latch member 218 and a substantially circular central boss zone 220 therebetween. First latch member 216 and second latch member 218 include a first latch groove 222 and a second latch groove 224, respectively, sized and adapted to rotatably receive and retain a portion of diametral or mounting bar 60 (FIG. 1) of tool 78. Advantageously, first latch groove 222 and second latch groove 224 are substantially parallel to each other and are substantially orthogonal to shaft axis 213.

Meanwhile, central boss zone 220 is sized and adapted to receive central disc 134 associated with diametral bar 60. First latch member 216 and second latch member 218, in addition to receiving respective portions of diametral bar 60, are configured to aid in the centering of central disc 134 on central boss zone 220 and thus in keeping central disc 134 substantially coaxial with shaft axis 213.

Second partial boss 206 has a first boss portion 226, an oppositely directed second boss portion 228 and a primary boss bore 230, primary boss bore 230 slidably accommodating driver shaft 202 therein. First boss portion 226 includes an inwardly tapered first extension member 232 and a diametrically opposed, inwardly tapered second extension member 234.

First extension member 232 and second extension member 234 are configured to coact with first latch member 216, second latch member 218 and central boss zone 220 of first partial boss 204 so as to form a bayonet latch mechanism 236, as best seen in FIGS. 16 and 18. Bayonet latch mechanism 236 has an axially extending, inwardly tapered latch bore 238 therein. Latch bore 238 extends coaxially from central boss zone 220 of first partial boss 204 and is configured to receive central disc 134 of diametral bar 134 and to thereby center tool 78 on driver shaft 202 relative to shaft axis 213. Another feature related to bayonet latch mechanism 236 is that first extension member 232 and second extension member 234 are configured for releasably locking diametral bar 60 in place, once such diametral bar 60 is rotated into both first latch groove 222 and second latch groove 224.

The interior of second boss portion 228 of second partial boss 206 is separated from first boss portion 226 thereof by primary boss bore 230. Second boss portion 228 has a spaced interior boss surface 240 that is spaced from and substantially parallel to driver shaft 202. An interior boss stop portion 242 is located at the junction of primary boss bore 230 and spaced interior boss surface 240, interior boss stop portion 242 advantageously being substantially orthogonal to driver shaft 202.

Shaft spring 208 is slidably mounted on driver shaft 202, at least a substantial portion of which is positioned between driver shaft 202 and spaced interior boss surface 240. Shaft spring 208 has a first spring end 244 and a second spring end 246. As seen from FIG. 16, first spring end 244 is biased against interior boss stop portion 242.

Driver sleeve 210 is slidably mounted on driver shaft 202, driver sleeve 210 having a sleeve operative position 248 relative thereto. Driver sleeve 210 includes a distal first sleeve end surface 250 and a distal second sleeve end surface 252. When sleeve operative 248 is assumed, first sleeve end surface 250 is held in contact with second spring end 246 of shaft spring 208 by the action of bias button 212 against second sleeve end surface 252. Further, driver sleeve 210 has a first sleeve end portion 254 and a second sleeve end portion 256 adjacent first sleeve end surface 250 and second sleeve end surface 252, respectively. Advantageously, at least first sleeve end portion 254 is sized and configured to be received between driver shaft 202 and spaced interior boss surface 240, thus permitting first sleeve end surface 250 to be more stably positioned against second spring end 246.

Bias button 212, as best seen in FIG. 19, is positioned within driver shaft 202 and biased so as to normally protrude therefrom. The position of bias button 212 is chosen such that second sleeve end surface 252 is immediately adjacent thereto when driver sleeve 210 is in sleeve operative position 248. Thus, bias button 212 is configured for releasably maintaining driver sleeve 210 in sleeve operative position 248. As seen from FIGS. 17 and 19, bias button 212 includes a movable button member 258 and a set screw 260 interconnected with a bias spring 262.

By the invention, there is provided a new and improved tool driver which can be used with rotary tools of all types, including acetabular cups, patella cutters, reamers and the like. The new and improved tool driver of the invention holds rotary tools coaxially of the longitudinal axis with preciseness such that all of the cutting edge of the rotary tools function as designed. The new and improved tool driver of the invention can be utilized with rotary tools of all sizes and can be used with rotary tools of the type which collect milled bone tissue and other debris for use as filler. The new and improved tool driver and the tools of the invention can be easily cleaned, sterilized and reused, are easy and convenient to use, and can be manufactured without holding any close tolerances and yet achieve exact coaxial rotation of the rotary tool.

While a specific embodiment of the invention has been shown and described herein for purposes of illustration, the protection afforded by any patent which may issue upon this application is not strictly limited to the disclosed embodiment; but rather extends to all structures and arrangements which fall fairly within the scope of the claims which are appended hereto:

What is claimed is:

1. A tool driver comprising a shaft having a longitudinal axis and opposite ends, a first partial boss at one of said shaft ends, a tool collet at the other of said shaft ends, a second partial boss having a bore extending therethrough, said second partial boss being positioned on said shaft with said shaft in said bore, a stop on said shaft, said second partial boss being slidable on said shaft between said first partial boss and said stop, a spring being positioned between said second partial boss and said stop, said spring urging said second partial boss into said engagement with said first partial boss, said first and second partial bosses being complementary to each other, said first and second partial bosses in engagement with each other defining a bayonet type latch mechanism, said latch mechanism having an axially extending inwardly tapered bore extending from said one end coaxially of said shaft into said first and second bosses, said tapered bore being adapted to receive a coaxially located disc of a tool to be connected to said tool driver within said tapered bore, said tapered bore and said tool disc coaxially centering said tool on said axis of said tool driver.

2. The tool driver of claim 1 wherein said stop being a removable stop on said shaft whereby said second partial boss and said stop and said spring may each be disassembled from said shaft when desired.

3. The tool driver of claim 1 wherein said bayonet type latch mechanism comprises a primary groove extending diametrically of said first boss, said primary groove having width sufficient to receive a mounting bar extending diametrically of a rotary tool to be positioned therein, and a secondary diametral groove circumferentially spaced therefrom, said secondary groove also having a width sufficient to receive said tool mounting bar therein, said primary groove having a bottom and upstanding sides and an open top, said second secondary groove having a bottom in the same plane as said primary groove bottom, one upstanding wall remote from said primary groove, and a top.

4. The tool driver of claim 3 wherein said second partial boss is also rotary slidable about said shaft and said longitudinal axis, said first and second partial bosses being engaged in non-complementary fashion at positions rotatably spaced from said complementary position, said secondary groove being open to receive said tool mounting bar therein.

5. The tool driver of claim 4 wherein said second partial boss includes a second spaced apart upstanding side of said secondary groove, said secondary groove being closed when said first and second partial bosses are in said complementary position.

6. The tool driver of claim 3 wherein said secondary groove is closed when said first and second partial bosses are engaged in said complementary position.

7. The tool driver of claim 3 wherein said secondary groove is open when said first and second bosses are spaced apart or engaged in said non-complementary positions.

8. The tool driver of claim 1 further comprising a lock preventing movement between said first and second partial bosses.

9. The tool driver of claim 8 wherein said lock locks only rotary movement between said first and second bosses.

10. The tool driver of claim 1 wherein said first partial boss also includes said axially extending tapered bore in said boss which receives a centrally located disk on a tool to be used with said tool driver.

11. The tool driver of claim 10 wherein said first and second partial bosses in said complementary position have a primary groove extending diametrically of said boss, said primary groove having a width sufficient to receive a mounting bar extending diametrically of a rotary tool to be positioned therein, and a secondary diametral groove radially spaced therefrom, said secondary groove also having a width sufficient to receive said tool mounting bar therein, said primary groove having a bottom upstanding side and an open top, said secondary groove having a bottom in the plane as said primary groove bottom, one upstanding side remote from said primary groove and a top.

12. The tool driver of claim 10 wherein said second partial boss includes a spaced apart opposite upstanding side of said secondary groove, said secondary boss in said complementary position closing said secondary groove.

13. The tool driver of claim 11 wherein said upstanding wall of said secondary groove of said secondary partial boss is tapered, said upstanding wall engages said tool mounting bar in said secondary groove and urges said mounting bar against said one upstanding side and said top.

14. The tool driver of claim 11 wherein said first partial boss includes both said tapered bore and said primary groove.

15. The tool driver of claim 11 wherein said first partial boss includes both said primary groove and said secondary groove, said primary groove being larger than said tool mounting bar whereby said tool mounting bar can be placed within said primary groove in more than one radial position.

16. The tool driver of claim 11 wherein said second partial boss both closes said second groove and limits the positioning of said tool mounting bar in said first groove to only be radially positioned in said second groove.

17. The tool driver of claim 11 wherein said secondary groove is closed in said complementary position.

18. The tool driver of claim 17 wherein said secondary groove is open in all non-complementary positions.

19. The tool driver of claim 18 further comprising a lock, said lock locking first and second partial bosses in said complementary position and in said open position.

20. The tool driver of claim 19 wherein said lock positions are radially spaced apart.

21. The tool driver of claim 1 wherein said first and second partial bosses combine to define an entry slot for properly positioning said tool mounting bar preparatory to entering said primary groove.

22. The tool driver of claim 21 wherein said entry slot also functions as said lock locking said part bosses in an open condition.

23. The tool driver of claim 18 wherein said tapered bore has a bottom in the same plane as said primary and secondary groove bottoms, said bore and said primary groove being both accessible from the distal end of said boss, whereby the diametrically extending mounting bar and disc of a tool may be positioned in said primary groove and bore and rotated a partial rotation into said secondary groove when said partial bosses are in said open condition.

24. The tool driver of claim 1 wherein said second partial boss is slidably positioned on said shaft and movable between an at rest position in which said second partial boss is complementary to said first part boss and positions remote therefrom, said second partial boss being urged toward said first partial boss.

25. The tool driver of claim 11 wherein said tapered bore is partially defined by said first partial boss and partially defined by said second partial boss.

26. The tool driver of claim 25 wherein said primary groove is in said first partial boss.

27. The tool driver of claim 26 wherein said secondary groove is in said first partial boss except for one upstanding wall.

28. The tool driver of claim 27 wherein said secondary groove bottom and said primary groove bottom are in the same plane.

29. The tool driver of claim 28 wherein said bore and said primary groove being both accessible from the distal end of said boss, whereby the diametrically extending mounting bar and disc of a tool may be positioned in said primary groove and bore and rotated a partial rotation into said secondary groove.

30. The tool driver of claim 1 wherein said bore is tapered adjacent said distal end.

31. The tool driver of claim 30 wherein said taper is more drastic adjacent said distal end than remote from said distal end.

32. The tool driver of claim 3 wherein said upstanding walls of said primary groove are tapered.

33. The tool driver of claim 3 wherein at least one wall of said secondary groove is tapered.

34. The tool driver of claim 3 wherein said wall of said secondary groove on said second partial boss is tapered.

35. The tool driver of claim 3 wherein said top is tapered with respect to said bottom.

36. The tool driver of claim 5 further comprising a tool having an open back, a bar diametrically extending across said open back of said tool, a disc on said bar coaxial of said cutting edge and medial of said bar ends, said bar being in said secondary groove and held fast between said secondary groove bottom and said secondary groove top and between said pin and said upstanding wall of said secondary groove.

37. The tool driver of claim 36 wherein said tool being maintained coaxially of said tool driver by the engagement between said disc and said tapered bore, said tool driver being prevented from rotating about said axis by engagement between said upstanding side of said secondary groove and said pin, said tool being incapable of axial movement of said tool driver by engagement between said secondary groove bottom and top, said tool being held against lateral or transverse movement of said tool driver by the engagement between said disc and said tapered bore.

38. The tool driver of claim 1 wherein said first partial boss and said second partial boss being approximately the same size.

39. The tool driver of claim 1 further comprising a handle on said shaft, said handle being freely rotatable about said shaft independently thereof.

40. A tool driver comprising:
- a driver shaft having a longitudinal shaft axis, said driver shaft having a first shaft end and a second shaft end, said driver shaft having a first partial boss at said first shaft end; and
- a second partial boss having a boss bore extending therethrough, said second partial boss being slidably mounted on said driver shaft, said first partial boss limiting movement of said second partial boss in one direction on said driver shaft, said first partial boss and said second partial boss being configured for engaging with each other so as to define a bayonet latch mechanism, said first partial boss including a first latch member and, spaced therefrom and diametrically opposed thereto, a second latch member, said second partial boss including an inwardly tapered first extension member and a diametrically opposed, inwardly tapered second extension member.

41. The tool driver of claim 40, wherein said bayonet latch mechanism has an axially extending latch bore therein, said latch bore extending coaxially from said first shaft end, said tool driver being configured for connecting with a tool having a diametrically extending mounting bar, the mounting bar having a central, coaxially located positioning disc associated therewith, said latch bore being configured to receive the positioning disc of the tool therein and to thereby center the tool on said driver shaft relative to said shaft axis.

42. The tool driver of claim 40, wherein said first latch member includes a first latch groove, said second latch member including a second latch groove, said first latch groove and said second latch groove each being substantially parallel to one another and substantially orthogonal to said shaft axis, said tool driver being configured for connecting with a tool having a diametrically extending mounting bar adapted for direct connection with said tool driver, each said first latch groove and said second latch groove being sized and adapted to receive the mounting bar of the tool therein.

43. The tool driver of claim 40, wherein said first extension member and said second extension member are configured for coacting with said first latch member and said second latch member to form a bayonet attachment with a tool carried by said tool driver.

44. A tool driver, comprising:
- a driver shaft having a longitudinal shaft axis, said driver shaft having a first shaft end and a second shaft end, said driver shaft having a first partial boss at said first shaft end; and
- a second partial boss having a boss bore extending therethrough, said second partial boss being slidably mounted on said driver shaft, said first partial boss limiting movement of said second partial boss in one direction on said driver shaft, said first partial boss and said second partial boss being configured for engaging with each other so as to define a bayonet latch mechanism, said second partial boss has a first boss portion configured for coacting with said first partial boss, said second partial boss further having an oppositely directed second boss portion, said boss bore extending between said first boss portion and said second boss portion, said second boss portion having a spaced interior boss surface spaced from said driver shaft, said second boss portion having an interior boss stop portion between said primary boss bore and said spaced interior boss surface;
- a shaft spring slidably mounted on said driver shaft, at least a portion of said shaft spring being positioned between said driver shaft and said spaced interior boss surface, said shaft spring having a first shaft spring end and a second shaft spring end, said first shaft spring end being biasedly positioned against said interior boss stop portion; and
- a driver sleeve slidably mounted on said driver shaft, said driver sleeve having a sleeve operative position relative to said driver shaft, said driver sleeve having a distal first sleeve end surface, said second shaft spring end being biasedly positioned against said first sleeve end surface when said driver sleeve is stationed in said sleeve operative position.

45. The tool driver of claim 44, further comprising a bias button positioned within said driver shaft and biased so as to normally protrude therefrom, said driver sleeve having a distal second sleeve end surface, said bias button being located so as to normally protrude immediately adjacent said second sleeve end surface when said driver sleeve is in said sleeve operative position.

46. The tool driver of claim 45, wherein said bias button contacts said second end sleeve surface when said driver sleeve is in said sleeve operative position and said bias button is protruding from said driver shaft.

* * * * *